United States Patent
Rosenberg

(10) Patent No.: US 7,662,768 B2
(45) Date of Patent: Feb. 16, 2010

(54) TRANSDIFFERENTIATION OF PANCREATIC ACINAR CELLS

(75) Inventor: Lawrence Rosenberg, Montreal (CA)

(73) Assignee: McGill University, Montreal, CA (US)

( * ) Notice: Subject to any disclaimer, the term of this patent is extended or adjusted under 35 U.S.C. 154(b) by 904 days.

(21) Appl. No.: 10/338,028

(22) Filed: Jan. 8, 2003

(65) Prior Publication Data

US 2003/0203850 A1     Oct. 30, 2003

Related U.S. Application Data

(60) Provisional application No. 60/346,890, filed on Jan. 11, 2002.

(51) Int. Cl.
*A61K 38/00* (2006.01)
*A61K 51/00* (2006.01)

(52) U.S. Cl. ............... 514/2; 530/326; 424/1.69

(58) Field of Classification Search ............ None
See application file for complete search history.

(56) References Cited

U.S. PATENT DOCUMENTS

| 5,834,590 | A | 11/1998 | Vinik et al. |
| 5,840,531 | A | 11/1998 | Vinik et al. |
| 2003/0138951 | A1 * | 7/2003 | Yin .................... 435/370 |

OTHER PUBLICATIONS

Bouwens L. "Transdifferentiation Versus Stem Cell Hypothesis for the Regeneration of Islet Beta-Cells in the Pancreas", 1998, Microscopy Research And Technique, vol. 43. pp. 332-336.*

Petropavlovskaia et al. "Development of an In Vitro Pancreatic Tissue Model to Study Regulation of Islet Neogenesis Associated Protein Expression", 2006, Journal of Endocrinology, vol. 191. pp. 65-81.*

Strumello. "Surprise: INGAP Moves Ahead!". http://sstrumello.blogspot.com/2008/03/surpise-ingap-moves-ahead.html. Wednesday, Mar. 19, 2008.*

Cell Differentiation Unit, Vrije Universiteit Brussel-Free University of Brussels, Brussels, Belgium, "Regulation of Pancreatic Beta-Cell Mass.". http://www.100md.com/html/DirDu/2006/10/18/25/69/17.htm (2006)).*

Yuan S. et al., "Phenotypic modulation of hamster acinar cells by culture in collagen matrix," Exp Cell Res. (Dec. 15, 1997); 237(2):247-258 (Abstract only).

Rafaeloff R. et al., "Cloning and Sequencing of the Pancreatic Islet Neogenesis Associated Protein (INGAP) Gene and Its Expression in Islet Neogenesis in Hamsters," J. Clin. Invest. (May 1997) vol. 99, No. 9, pp. 2100-2109.

Mendosa, R., "INGAP Peptide," www.mendosa.com/ingap.htm, 2002.

* cited by examiner

*Primary Examiner*—Maury Audet
(74) *Attorney, Agent, or Firm*—Banner & Witcoff, Ltd.

(57) ABSTRACT

Pancreatic acinar cells contribute to β-cell neogenesis. Hamsters administered pentadecapeptide of INGAP protein demonstrated a 2-fold increase in the number of extra-islet acinar-associated β-cell clusters resulting in a 2.8-fold increase in the overall extra-islet β cell mass as compared to controls. In mammals acinar-to-β-cell differentiation provides an alternate pathway to β-cell neogenesis; INGAP peptide plays a significant role in this process.

17 Claims, 6 Drawing Sheets

Fig. 2
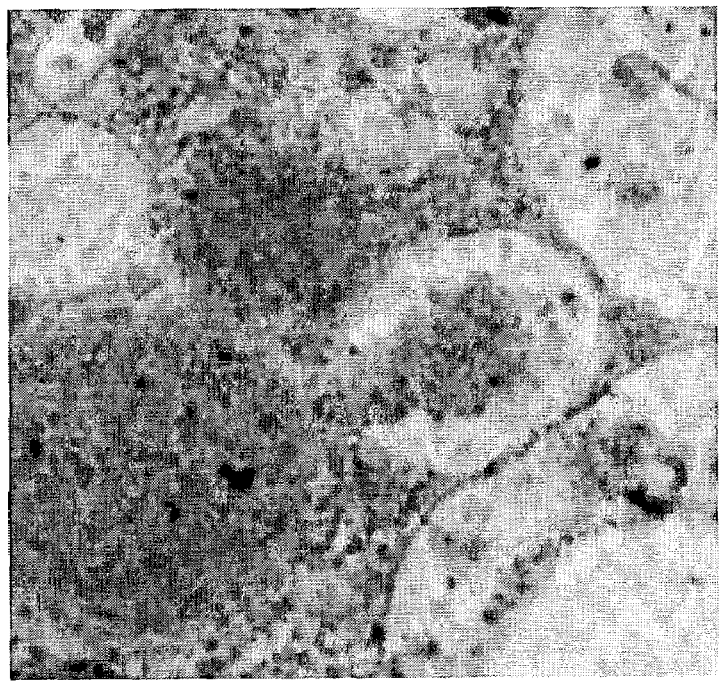
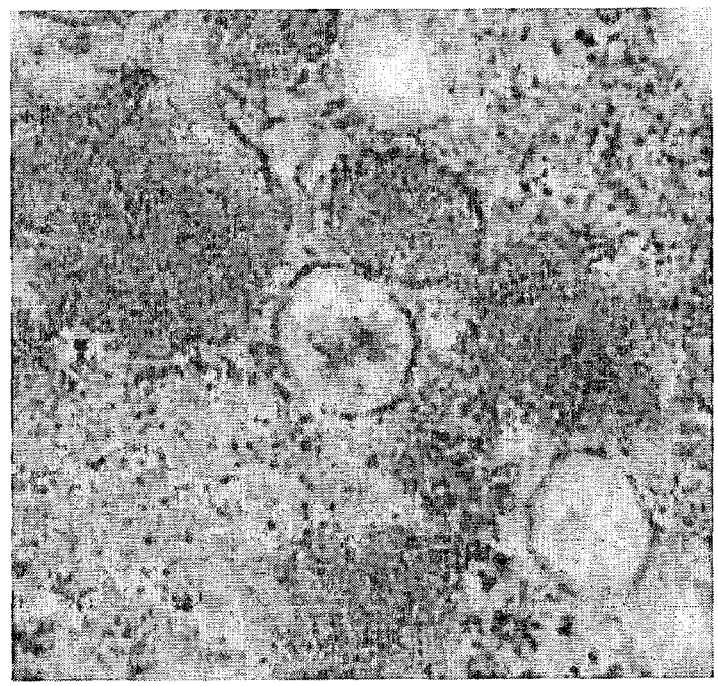

Fig. 6
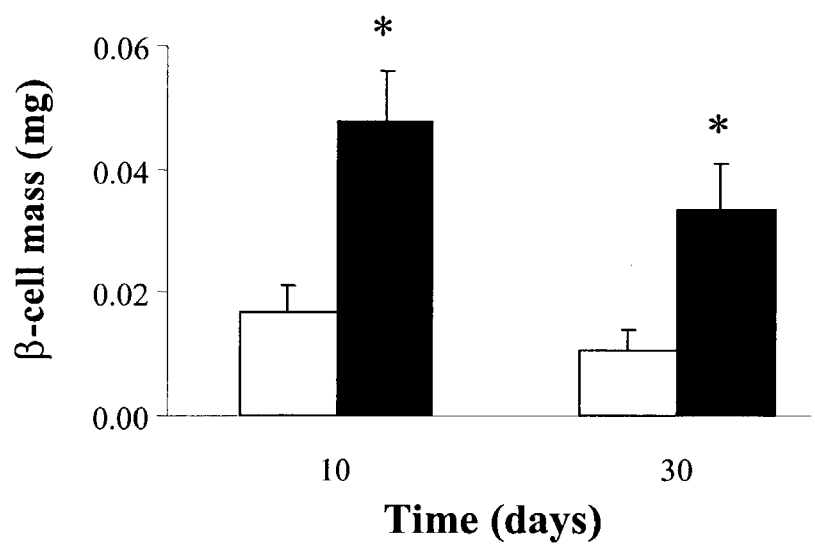
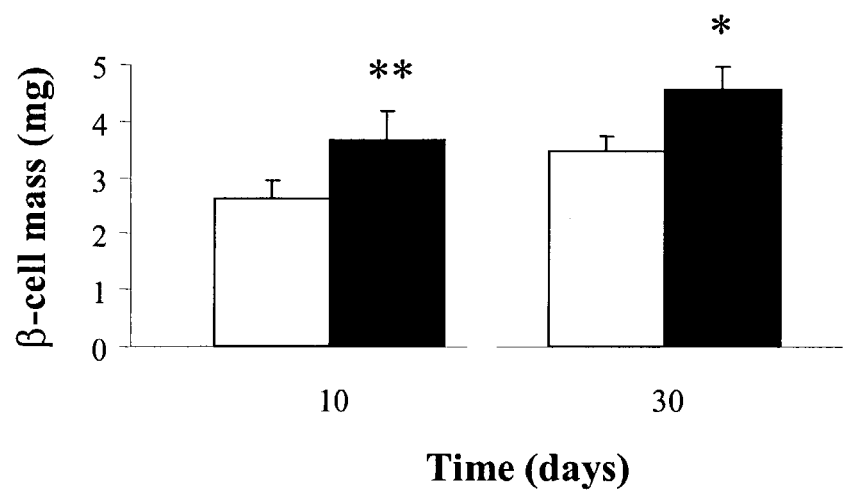

SEQUENCE LISTING

<160> NUMBER OF SEQ ID NOS: 1

<210> SEQ ID NO 1
<211> LENGTH: 15
<212> TYPE: PRT
<213> ORGANISM: Homo sapiens

<400> SEQUENCE: 1

Ile Gly Leu His Asp Pro Ser His Gly Thr Leu Pro Asn Gly Ser
1               5                   10                  15

TRANSDIFFERENTIATION OF PANCREATIC ACINAR CELLS

This application claims priority to provisional U.S. Application Ser. No. 60/346,890 filed Jan. 11, 2002.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The invention relates to the area of diabetes and beta cell insufficiency. It relates to in vivo methods for increasing beta cell mass and number by transdifferentiation.

BACKGROUND OF THE INVENTION

It has long been known that β-cell neogenesis, new β-cell formation from non β-cell precursors, could result in expansion of the β-cell mass (1). Only recently has induction of β-cell neogenesis received attention as a therapy for diabetes mellitus. As the wealth of information about β-cell neogenesis increases, general ideals form about the type of tissue and by what means these tissues are involved. Unfortunately, since β-cell neogenesis is a dynamic process, and we can only measure β-cell mass once for each subject, it is not easy to measure β-cell neogenesis. The current hallmark of β-cell neogenesis is endocrine cells budding from ductal structures (2). From an immunohistochemical position, it is very easy to record and quantify duct associated β-cell neogenesis. Because of this, less interest has been focused on the possibility of other pancreatic tissues giving rise to new β-cells.

The adult pancreas is approximately 80-85% acinar tissue, 15-20% duct tissue and 1 2% endocrine tissue. Based on this tissue division, acinar tissue could potentially be a large source of neogenic β-cell. The same difficulties exist in determining acinar-to-β-cell transdifferentiation as measuring duct-associated neogenesis. However, because islets are not normally found proximal to ducts, duct-associated β-cell neogenesis garners more credibility than acinar-associated β-cell neogenesis, where mature islets are normally found. Since mature islets consist of a central core of β-cells surrounded by a mantel of α, δ and PP cells, one way to quantify acinar-to-β-cell neogenesis is to determine the number of single insulin positive cells or small cell clusters devoid of any other endocrine cells (suggesting recent formation), that are associated with acinar tissue. Likewise, analyzing the co-localization of acinar and endocrine granules can also be used to suggest the occurrence of acinar-to-β-cell neogenesis.

BRIEF SUMMARY OF THE INVENTION

The present invention provides a method for inducing beta cell production in a mammal. An effective amount of INGAP pentadecapeptide, INGAP protein, or an active portion thereof, is delivered locally to acinar cells of a mammal. The acinar cells transdifferentiate and acquire the characteristics of beta cells.

In one of the embodiments of the invention, novel in vitro methods are contemplated to transdifferentiate non-beta cells of the pancreas into insulin-secreting functional islets. A small pancreatic tissue sample can be excised from a mammal, such as a human. The pancreatic tissue would essentially consist of acinar cells (about 80%), although small amounts of ductal epithelial cells, and perhaps islet cells, such as alpha and beta cells may also be present. Preferably the acinar cells comprise at least 50%, 60%, 60%, 80%, 90%, or 95% of the cell mass. The tissue sample is then incubated under appropriate conditions of temperature and humidity in the presence of INGAP or INGAP peptide and other necessary physiological growth factors that may support survival, growth, and differentiation of pancreatic cells. Transdifferentiation may be monitored with routine microscopic, histochemical, and biochemical techniques to ascertain the conversion of non-beta cells into functional islets. Once a necessary critical cell mass is achieved, the functional islets can then be transplanted into a mammal in need of such an endocrine pancreatic transplant. The functional islets will adapt physiologically and regulate carbohydrate metabolism. The transplant-receiving mammal may need to be treated with INGAP peptide, other growth factors, and/or immunosuppressants either before or after receiving the transplant.

BRIEF DESCRIPTION OF THE DRAWINGS

FIG. 2 shows an electron micrograph of blended acinar/islet tissue from PDO hamsters.

FIG. 6A shows extra-islet acinar-associated β-cell mass from INGAP peptide treated hamsters. FIG. 6B shows total β-cell mass from INGAP peptide treated hamster

DETAILED DESCRIPTION OF THE INVENTION

Figure 1:
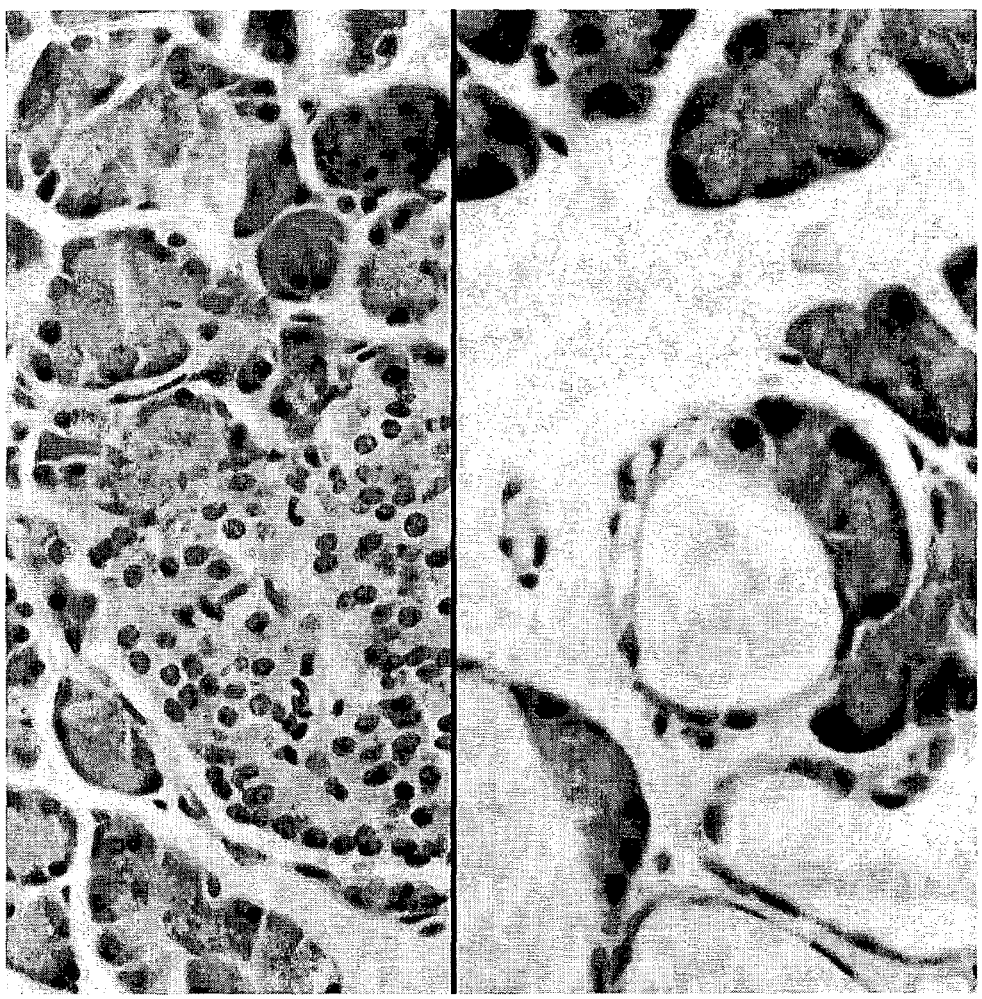
FIG. 1 shows a photomicrograph of acinar to endocrine and acinar to duct differentiation in PDO hamsters.

Previously, it has been considered that INGAP acts to stimulate ductal cells to differentiate to become beta cells. We have now discovered that INGAP also acts to stimulate acinar cells to transdifferentiate. Since acinar cells are far more numerous that ductal cells, this creates a huge reservoir for making beta cells. These beta cells can be used inter alia for transplantation. They can also improve the glycemic status of the treated mammal or person.

Moreover, the susceptibility of acinar cells to INGAP permits the treatment of individuals whose ductal cells are so severely diseased that they are not viable for transdifferentiation or whose ductal cells are otherwise non-responsive to INGAP, whether due to a genetic defect or to a disease process.

Local drug delivery procedures can obviate some of the problems associated with systemic therapies, including metabolic breakdown and side effects affecting efficacy. By presenting therapeutic concentrations of a drug only to the target site, minimizing effects upon non-target tissues, these problems can be obviated or minimized. The reduction in quantity of a drug required can also result in lower treatment costs.

Recognition of the advantages for local delivery strategies has stimulated the development of a number of catheter-based and patch-based delivery devices which apply drugs directly to body tissues at certain locations, often to sites that would be otherwise inaccessible without surgery. Delivery can be stimulated by application of radiation or an electrical current or gradient. Catheters or stents can also be used to accomplish the localized delivery. Percutaneous delivery by injection can also be used to achieve local delivery; preferably the injection is radiologically guided. Receptor targeted delivery can also be used for local delivery. Ligands for receptors on the cells of interest can be attached directly to the therapeutic agent, e.g., INGAP, or ligands can be attached to a vehicle, such as a liposome, microsphere, or polymer. Attachment can be covalent or non-covalent. Fusion proteins can be used which comprise INGAP and a cell specific ligand. Cannulae can also be used for local delivery. In some situations, the local delivery can be accomplished intraoperatively, for example by implantation of pellets or other slow delivery device directly at the desired site in the body. In still another method of accomplishing localized delivery, an INGAP expression construct can be administered which is transcriptionally active in acinar cells but not in ductal cells.

An ultrasound device can be used to facilitate local delivery of INGAP. In one example, a therapeutic drug delivery system for site-specific delivery of therapeutics employs microspheres that are filled with INGAP, typically in the form of a gas or liquid, but possibly a solid.

Microspheres can be introduced systemically into a patient's body, such as by intravenous injection. INGAP within the microspheres can be targeted to specific tissues through the use of ultrasonic energy. The ultrasonic energy is directed to the target area and causes the microspheres to rupture and release the therapeutic substance. This method for delivery permits one to control the delivery of therapeutic substances to a targeted tissue-of-interest, i.e., the acinar cells of the pancreas. This method also permits temporal and dosage control. Microspheres containing INGAP can be administered to a patient and the microspheres can be monitored by, for example, imaging to determine whether the microspheres are present within the tissue-of-interest. When present in the proper location, the microspheres can be ruptured using ultrasound to release the therapeutic substance into the tissue-of-interest.

The term INGAP is used herein to denote the full INGAP protein, no matter how made. The protein can be, e.g., harvested from a mammal or a human or synthesized in a recombinant cell. The term INGAP also includes INGAP pentadecapeptide, an active portion of the full length protein which comprises the amino acids Ile-Gly-Leu-His-Asp-Pro-Ser-His-Gly-Thr-Leu-Pro-Asn-Gly-Ser (SEQ ID NO: 1). Other active portions of full length INGAP are also contemplated with the meaning of this term. It is fully expected that active portions will overlap with the pentadecapeptide. But they may be larger or smaller. It is a matter of routine skill in the art to test candidate portions to determine if they have the biological activity of INGAP. Assays for such activity are known in the art. One such assay is the ability to induce transdifferentiation of acinar cells, as described below.

Although local delivery means are preferred, one can also deliver INGAP protein and related polypeptides by other means. These include intravenous, subcutaneous, intramuscular, intraperitoneal, transdermal, subdermal, inhalation, and per os. Typical dosages which can be used for delivery to a patient ranges from about 0.1 to 900 mg. As mentioned above, local delivery often reduces the amount of drug which must be delivered as compared to systemic administration means. Agents can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, rectal, or pancreatic duct retrograde perfusion. Agents for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the mammal. Agents for intravenous, intramuscular, intra-arterial, transdermal, and subcutaneous injections can be formulated using pharmaceutically acceptable carriers well known in the art in dosages suitable for injection into the mammal. Agents for intranasal, topical, and rectal administration can be formulated using pharmaceutically acceptable carriers well known in the art in dosages suitable for surface administration to the mammal. Mammals in need of transdifferentiation of non-beta cells to beta cells include for example, mammals with diabetes mellitus, impaired glucose tolerance, impaired fasting glucose, hyperglycemia, obesity, and pancreatic insufficiency. Mammals in need of a decrease in INGAP expression include for example, mammals with hypoglycemia.

The hallmark of transdifferentiated acinar cells is that they produce insulin and form endocrine granules. Thus they acquire the defining features of beta cells. These qualities can be assessed by any techniques known in the art, including immunohistochemistry, histochemistry, and ultrastructural observation.

EXAMPLES

Example 1—Partial Duct Obstruction

Fourteen female Syrian hamsters (Charles River, Quebec), 8 weeks of age, were anesthetized and a midline laparotomy incision was made. The head of the pancreas was exposed and a 2 mm wide piece of cellophane tape (Imperial Tobacco, Montreal, QC) was wrapped around the pancreas and fixed in position. Two weeks following partial duct obstruction (PDO), hamsters were injected with 2 µCi of tritiated thymidine ($^3$H-TdR) and were then sacrificed either one hour (n=7) or six weeks (n=7) later. At the time of sacrifice animals were anesthetized and a pancreatectomy was performed. Tissues were fixed either in formalin and processed for autoradiography, or 1% glutaraldehyde and 4% formaldehyde in 200 mOsm phosphate buffer and processed for electron microscopy.

The percentage of cells replicating was determined by counting a minimum of 5000 cells per animal. Briefly, acinar and endocrine cells were determined to be positive for the incorporation of $^3$H-TdR if five or more silver granules were found on the nucleus. Acinar and endocrine cell labelling indices were counted from seven animals at each time point.

Sections from Epon blocks were cut using a Reichert ultramicrotome, stained with toluidine blue and examined with a Philips electron microscope. Areas of interest were identified and EM photomicrographs were recorded.

Cellular differentiation was noted in pancreatic samples from partial duct obstructed hamsters (FIG. 1). There was a blending of the acinar and endocrine borders suggestive of acinar-to-endocrine differentiation. Upon further examination of these areas by electron microscopy, it was noted that there was co-localization of insulin granules and exocrine zymogen granules again supporting the notion of acinar to endocrine differentiation (FIG. 2).

Figure 3:
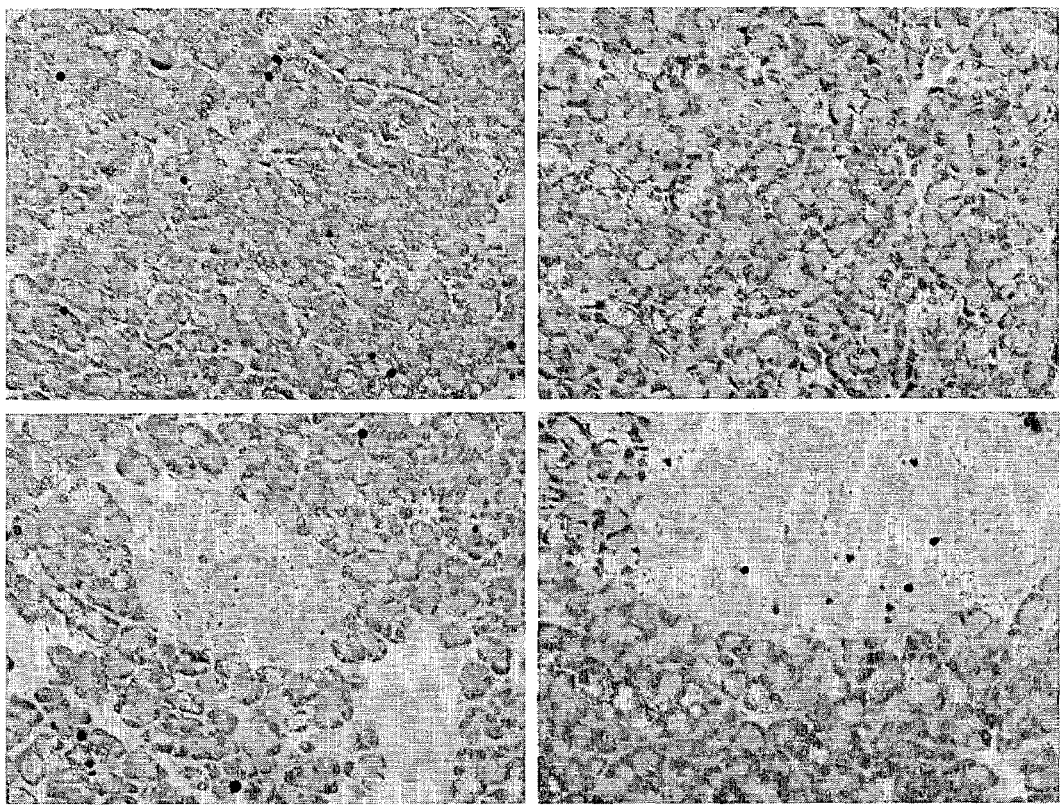
FIG. 3 shows a photomicrograph of $^3$H-TdR incorporation into acinar and endocrine tissues at 2 (left) and 8 weeks (right) following PDO.
Figure 4:
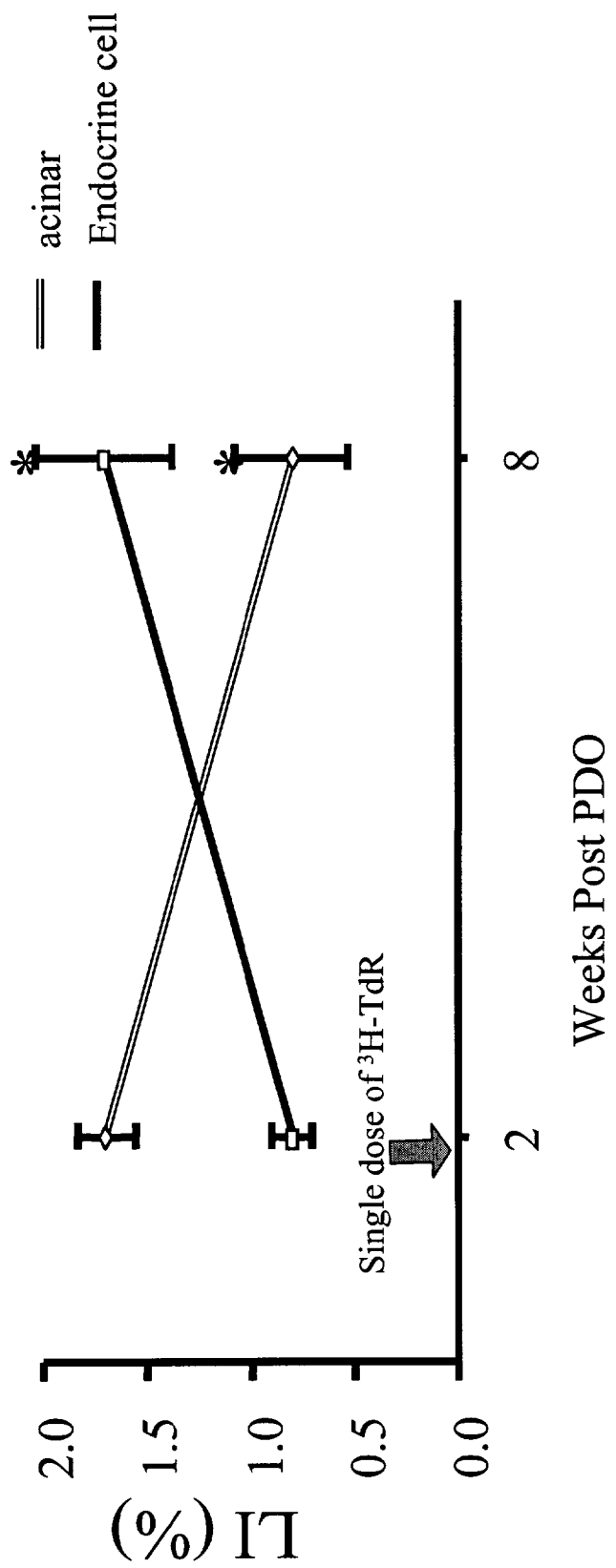
FIG. 4 shows acinar and endocrine cell labelling indices from PDO hamsters

To quantify further the potential differentiation of acinar tissue to endocrine cells we examined the incorporation of $^3$H-TdR into both acinar and endocrine cells at two weeks and eight weeks following partial duct obstruction (FIG. 3). $^3$H-TdR incorporation into acinar cells was highest at 2 weeks after PDO (1.70±0.14%) and declined to 0.80±0.27% at 8 weeks after PDO (p=0.025) (FIG. 4). Incorporation of $^3$H-TdR into endocrine cells was inversely related to that observed in acinar cells. Two weeks following PDO, endocrine cell $^3$H-TdR uptake was 0.80±0.26 and it increased to 1.7±0.08 (p<0.001) at 8 weeks after PDO.

Example 2—INGAP Peptide Administration

Female Syrian hamsters, 8 weeks of age, were randomly allocated to receive daily intra-peritoneal injections of INGAP peptide (Ile-Gly-Leu-His-Asp-Pro-Ser-His-Gly-Thr-Leu-Pro-Asn-Gly-Ser) (250 µg twice daily) (SEQ ID NO: 1) or an equivalent volume of saline for either 10 (saline n=10, INGAP n=15) or 30 (S n=10, I n=15) days. At the end of the study period, animals were sacrificed by bleeding, and the pancreata excised through a midline laparotomy incision, for morphologic and morphometric analysis.

Samples were embedded in paraffin wax and 4 µm-thick sections were cut. The sections were processed for routine histology and immunostained for insulin, CK19 (1:750, 1:100 respective antibody dilution, Dako Corp., Santa Barbara, Calif.), glucagon, somatostatin and pancreatic polypeptide (1:750 antibody dilution, Biogenex, San Ramon, Calif., USA), using the AB complex method (streptavidin-biotin horseradish peroxidase complex, Dako Corp., Santa Barbara, Calif.), as described previously (22). A rabbit PDX-1 antibody directed against the $NH_2$-terminus of the frog homologue of the protein encoded by the pdx-1 gene was used as the primary antibody (1:750 dilution; a gift from C. Wright, Vanderbilt University). Slides were countered stained with Harris hematoxylin (Sigma, St. Louis, Mo.).

Comparison between groups was done using 1-way ANOVA, 2-way ANOVA with post hoc one-tail t-test or $X^2$ analysis where appropriate. Data are presented as mean±SEM. Significance was accepted at the 5% level.

To determine β-cell mass (mg/pancreas), each gland was sectioned along its longitudinal axis to avoid any sampling bias due to regional variation in islet distribution and cell composition. Islet cross-sectional areas were traced manually with the aid of an Olympus BX60 microscope connected by video camera to a computer equipped with Image-pro Plus software version 4.0 (23). The total β-cell mass was calculated by a stereological equation, as described previously (22).

β-cell neogenesis and acinar-associated β-cell mass was analysed as described previously. Briefly, extra-islet acinar-associated β-cells/cell clusters were defined as insulin positive cells/cell clusters not associated with any other endocrine cells (α, δ, PP), completely surrounded by acinar tissue and a minimum of 100 µm from ductular tissue. The percent β-cell area being extra-islet acinar-associated was determined and multiplied by the weight of the excised organ to determine extra-islet acinar-associated β-cell mass.

Figure 5:
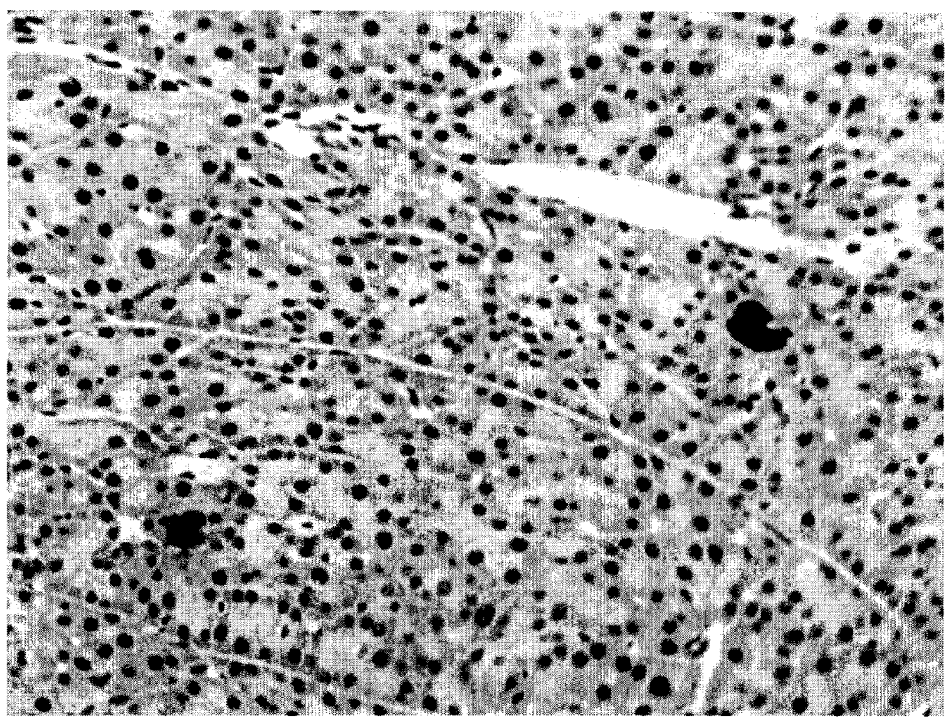
FIG. 5 shows photomicrograph of extra-islet acinar-associated β-cells

Administration of INGAP peptide is known to stimulate β-cell mass expansion through the process of duct-to-β-cell differentiation. In this study we determined the ability of INGAP peptide to stimulate acinar differentiation. Following 10 days of INGAP peptide treatment there was a 180% increase in extra-islet acinar-associated β-cell mass, and following 30 days of treatment there was a 200% increase versus saline infused controls (p<0.05) (FIG. 5a). Along with the increase in extra-islet acinar-associated β-cell mass there was an increase in total β-cell mass in these animals by 44% following 10 days and 31% by 30 days (FIG. 5b).

These results support acinar-to-β-cell differentiation as an alternate pathway to β-cell neogenesis, thereby highlighting the inherent plasticity of the adult pancreas, and support a role for INGAP in this process.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

I claim:

1. A method of inducing beta cell production in a mammal, comprising: locally delivering an effective amount of INGAP pentadecapeptide, INGAP protein, or a portion of the INGAP protein, wherein said portion comprises the INGAP pentadecapeptide, to acinar cells of a mammal, whereby the acinar cells transdifferentiate.

2. The method of claim 1 wherein the transdifferentiated cells produce insulin.

3. The method of claim 1 wherein the transdifferentiated cells form endocrine granules.

4. The method of claim 1 wherein the step of locally delivering is performed by administering microspheres.

5. The method of claim 4 wherein the microspheres are receptor-targeted.

6. The method of claim 4 wherein the microspheres are locally ruptured using ultrasonic energy to release INGAP pentadecapeptide, INGAP protein, or said portion.

7. The method of claim 1 wherein the step of delivering is performed by catheter.

8. The method of claim 1 wherein the step of delivering is performed by stent.

9. The method of claim 1 wherein the step of delivering is performed by percutaneous delivery.

10. The method of claim 1 wherein the step of delivering is performed by cannula.

11. The method of claim 1 wherein the step of delivering is performed intraoperatively.

12. The method of claim 1 wherein the step of delivering is performed by implantation of pellets containing INGAP pentadecapeptide, INGAP protein, or said portion.

13. The method of claim 1 wherein the step of delivering is performed by delivering an expression construct which is transcriptionally active in acinar cells but not in ductal cells.

14. The method of claim 1 further comprising the step of: harvesting transdifferentiated cells for use in transplantation.

15. The method of claim 1, wherein beta cell production is induced in a mammal by local delivery of the effective amount of the INGAP pentadecapeptide.

16. The method of claim 1, wherein beta cell production is induced in a mammal by local delivery of the effective amount of the INGAP protein.

17. The method of claim 1, wherein beta cell production is induced in a mammal by local delivery of the portion of the INGAP protein, wherein said portion comprises the INGAP pentadecapeptide.

* * * * *

UNITED STATES PATENT AND TRADEMARK OFFICE
CERTIFICATE OF CORRECTION

PATENT NO. : 7,662,768 B2 Page 1 of 1
APPLICATION NO. : 10/338028
DATED : February 16, 2010
INVENTOR(S) : Lawrence Rosenberg It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1336 days.

Signed and Sealed this

Thirtieth Day of November, 2010

David J. Kappos
*Director of the United States Patent and Trademark Office*